(12) United States Patent
Warren

(10) Patent No.: US 6,495,696 B1
(45) Date of Patent: Dec. 17, 2002

(54) METHOD AND APPARATUS FOR THE PREPARATION OF KETONES

(75) Inventor: Jack S. Warren, Blountville, TN (US)

(73) Assignee: EagleView Technologies, Inc., Minneapolis, MN (US)

( * ) Notice: Subject to any disclaimer, the term of this patent is extended or adjusted under 35 U.S.C. 154(b) by 0 days.

(21) Appl. No.: 10/143,443

(22) Filed: May 10, 2002

Related U.S. Application Data

(62) Division of application No. 09/394,583, filed on Sep. 13, 1999, now Pat. No. 6,392,099.
(60) Provisional application No. 60/109,261, filed on Nov. 19, 1998.

(51) Int. Cl.$^7$ ............................................. C07D 261/08
(52) U.S. Cl. ......................................................... 548/248
(58) Field of Search ........................................ 548/248

(56) References Cited

U.S. PATENT DOCUMENTS

| | | |
|---|---|---|
| 3,410,909 A | 11/1968 | Fleischer et al. |
| 3,453,331 A | 7/1969 | Hargis et al. |
| 3,466,334 A | 9/1969 | Young et al. |
| 3,660,491 A | 5/1972 | Thigpen et al. |
| 3,966,822 A | 6/1976 | Fukui et al. |
| 4,060,555 A | 11/1977 | Peterson et al. |
| 4,505,738 A | 3/1985 | Gsell |
| 4,515,626 A | 5/1985 | Szczepanski |
| 4,528,400 A | 7/1985 | Cryberg et al. |
| 4,570,021 A | 2/1986 | Cryberg et al. |
| 4,590,292 A | 5/1986 | Blackwell et al. |
| 4,693,745 A | 9/1987 | Brunner |
| 4,797,152 A | 1/1989 | Brunner |
| 4,803,268 A | 2/1989 | Brunner et al. |
| 4,872,902 A | 10/1989 | Brunner |
| 4,874,899 A | 10/1989 | Hoelderich et al. |
| 4,883,878 A | 11/1989 | Amato et al. |
| 4,964,846 A | 10/1990 | Gais et al. |
| 5,026,916 A | 6/1991 | Tobler |
| 5,124,293 A | 6/1992 | Lindfors et al. |
| 5,366,957 A | 11/1994 | Cain et al. |
| 5,434,152 A | 7/1995 | Huffman et al. |
| 5,453,545 A | 9/1995 | Burello et al. |
| 5,565,399 A | 10/1996 | Fraenkel et al. |
| 5,629,455 A | 5/1997 | Kaufhold et al. |
| 5,656,573 A | 8/1997 | Roberts et al. |
| 5,849,928 A | 12/1998 | Hawkins |
| 5,877,330 A | 3/1999 | Kishimoto et al. |
| 6,087,538 A | 7/2000 | Teles et al. |

FOREIGN PATENT DOCUMENTS

| | | |
|---|---|---|
| DE | 36 37 788 A1 | 5/1988 |
| DE | 197 26 666 A1 | 12/1998 |
| EP | 0 085 996 A2 | 8/1983 |
| EP | 0 418 175 B1 | 3/1991 |
| EP | 0 507 013 B1 | 10/1992 |
| EP | 0 527 036 B1 | 2/1993 |
| EP | 0 527 037 B1 | 2/1993 |
| EP | 0 560 482 B1 | 9/1993 |
| EP | 0 609 798 A1 | 8/1994 |
| EP | 0 682 659 B1 | 11/1995 |
| GB | 1 435 639 | 5/1976 |
| WO | WO 99/02476 | 1/1999 |
| WO | WO 99/24409 | 5/1999 |

OTHER PUBLICATIONS

G.W. Cannon et al., "Acylation Studies. I Methyl Cyclopropyl Ketone," *Journal of Organic Chemistry*, 17(5):685–692 (May 1952).
International Search Report for PCT/US99/25372 (2 pages), (Apr. 2000).
International Search Report for PCT/US00/24458 (6 pages), (Dec. 2000).
Rhone–Poulenc, Balance (TM) WDG Herbicide, Material Safety Data Sheet prepared Sep. 3, 1998 (7 pages).

*Primary Examiner*—Sreeni Padmanabhan
(74) *Attorney, Agent, or Firm*—Popovich & Wiles, P.A.

(57) ABSTRACT

A process for the preparation of a compound of formula (I)

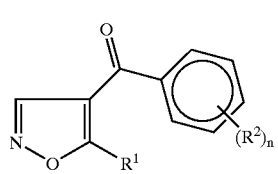

(I)

wherein:

$R^1$ is cycloalkyl having from three to six ring carbon atoms which is unsubstituted or which has one or more substituents selected from the group consisting of $R^4$ and halogen.

42 Claims, 1 Drawing Sheet

METHOD AND APPARATUS FOR THE PREPARATION OF KETONES

This application is a division of U.S. Ser. No. 09/394,583, filed Sep. 13, 1999, now U.S. Pat. No. 6,392,099, and this application claim benefit of provisional application U.S. Ser. No. 60/109,261, filed Nov. 19, 1998, the contents of each of which are hereby incorporated herein by reference.

BACKGROUND OF THE INVENTION

1. Field of the Invention

The present invention relates generally to the preparation of ketones and more particularly to a method and apparatus for preparing unsymmetrical ketones such as methyl cyclopropyl ketone (MCPK). The invention also relates to a method of using such ketone preparation method in the preparation of a herbicidal or other agricultural compounds.

2. Description of the Prior Art

In general, unsymmetrical ketones are useful as intermediates for the production of numerous specialty chemicals. More specifically, methyl cyclopropyl ketone (MCPK) has a variety of current and potential future uses including, among others, the production of specialty agricultural and pharmaceutical compounds.

Numerous literature references cite and disclose various well-known processes for the preparation of ketones. These processes include oxidation of secondary alcohols, Friedel-Crafts acylation, reaction of acid chlorides with organo cadmium compounds, acetoacetic ester synthesis and decarboxylation from acids, among others.

Text and literature references also detail problems associated with using these processes to produce ketones. These include problems such as the unavailability and/or cost of raw materials, the requirement of multi-stage processing, the low conversion of the raw materials and/or the low selectivity of the desired ketones, and the production of corrosive or hard to separate products.

Ketone production processes have also been described in the patent literature. For example, U.S. Pat. Nos. 4,528,400 and 4,570,021 disclose a process for the preparation of unsymmetrical ketones by a catalytic vapor phase reaction using reactants such as ketones with carboxylic acids. However, laboratory trials using acetone and cyclopropanecarboxylic acid resulted in the production of high quantities of gamma-butyrolactone, several pentenones and pentanones, but no MCPK.

U.S. Pat. Nos. 3,410,909 and 3,453,331 disclose processes for the preparation of symmetrical and unsymmetrical ketones from aldehydes containing up to 8 carbons in a non-cyclic saturated aliphatic chain.

German Patent Disclosure No. P36 37 788.0 (1986) discloses a specific condensation reactor process for the preparation of methyl cyclopropyl ketone (MCPK) from cyclopropanecarboxylic acid or its derivatives. However, although examples from this patent show raw material conversion of from 58 to 99 percent and selectivity to MCPK of 42 to 75 percent, the liquid hourly space velocity (LHSV) or weight hourly space velocity (WHSV) values of less than 1 (i.e., 0.25 to 0.99) minimize the industrial usefulness of this condensation reactor process.

European Patent Application No. 0 085 996 also discloses processes for the preparation of unsymmetric aliphatic ketones at atmospheric pressures (or slightly above) and at relatively low WHSV.

Still further, a reported disadvantage of all vapor phase tube reactor processes is the "coking" or deactivation of the catalyst and consequential "plugging" of the reactors. This results in the loss of production hours while the catalyst is being regenerated or replaced.

Accordingly, there is a need in the art for a method and apparatus for the production of ketones, and particularly unsymmetrical ketones such as methyl cyclopropyl ketone (MCPK) which utilizes readily available and inexpensive raw materials, which eliminates or minimizes reactor plugging, which provides for high conversion rates and high selectivity to MCPK and which dramatically improves the rate of production.

SUMMARY OF THE INVENTION

In contrast to the prior art, the present invention relates to a method and an apparatus for producing ketones, and in particular unsymmetrical ketones such as MCPK which overcome the limitations of the prior art. Specifically, the method and apparatus of the present invention utilizes readily available and inexpensive raw materials, minimizes reactor plugging, results in high conversion and selectivity rates and provides for increased production of the desired ketone. Generally, the raw materials used in the method and apparatus of the present invention include an acid or aldehyde or their derivatives and a carboxylic acid.

More specifically, the present invention involves the preparation of methyl cyclopropyl ketone (MCPK) utilizing a tube reactor provided with a suitable catalyst ranging from about 1 percent to 25 percent by weight. The preferred raw materials or feed materials include cyclopropylaldehyde or its derivatives (such as cyclopropanecarboxylic acid) and acetic acid which are readily available through processes known in the art. These raw materials are fed into a catalytic tube reactor where they are exposed to the catalyst and react to produce the desired ketone and various co-products. Preferably, the new raw materials are fed from the bottom to the top so that the reactant materials flow vertically upwardly through the reactor. To minimize undesired co-products as well as "coking" of the catalyst and thus "plugging" of the reactor, the optimum reaction temperature of the reactant feed stream is determined and the catalyst bed is preheated to such optimum temperature prior to the introduction of the reactant materials.

To further minimize downtime of the production process during the regeneration of catalyst or during reactor maintenance or repair, multiple or side-by-side reactors are provided with means for selectively directing the reactant materials to one or the other and removing product and co-products from such selected reactor. This permits the non-selected reactor or reactors to be repaired and/or maintained and the catalyst therein to be regenerated, if needed.

In the preferred embodiment and method of the present invention, the reactor is a vapor phase tube reactor in contrast to a condensation reactor or a batch stirred reactor. Further, the reactant materials in the method and apparatus of the present invention are preferably fed into the bottom of the reactor and caused to flow upwardly through the reactor over the catalyst. With this configuration, it is possible to dramatically increase the LHSV or WHSV. This results in dramatically increased production rates.

Accordingly, an object of the present invention is to provide an improved method and apparatus for the preparation of ketones and in particular unsymmetrical ketones such as methyl cyclopropyl ketone (MCPK).

Another object of the present invention is to provide a method and apparatus for preparing MCPK in a tube reactor with a minimized incidence of reactor plugging.

Another object of the present invention is to provide a method and apparatus for the preparation of MCPK utilizing inexpensive and readily available reactant or feed materials.

A further object of the present invention is to provide an improved method and apparatus for the preparation of MCPK at high conversion rates and high selectivity to MCPK, with minimal undesirable co-products.

A still further object of the present invention is to provide a method and apparatus for the preparation of MCPK at high production rates so as to result in an economically attractive process.

A still further object of the present invention is to provide a method of using the above-described ketone preparation method to prepare a herbicidal or other agricultural compound.

These and other objects of the present invention will become apparent with reference to the drawing, the description of the preferred embodiment and the appended claims.

DESCRIPTION OF THE DRAWING

The single FIGURE is a schematic illustration of the method and apparatus of the present invention.

DESCRIPTION OF THE PREFERRED EMBODIMENT AND METHOD

Figure 1:
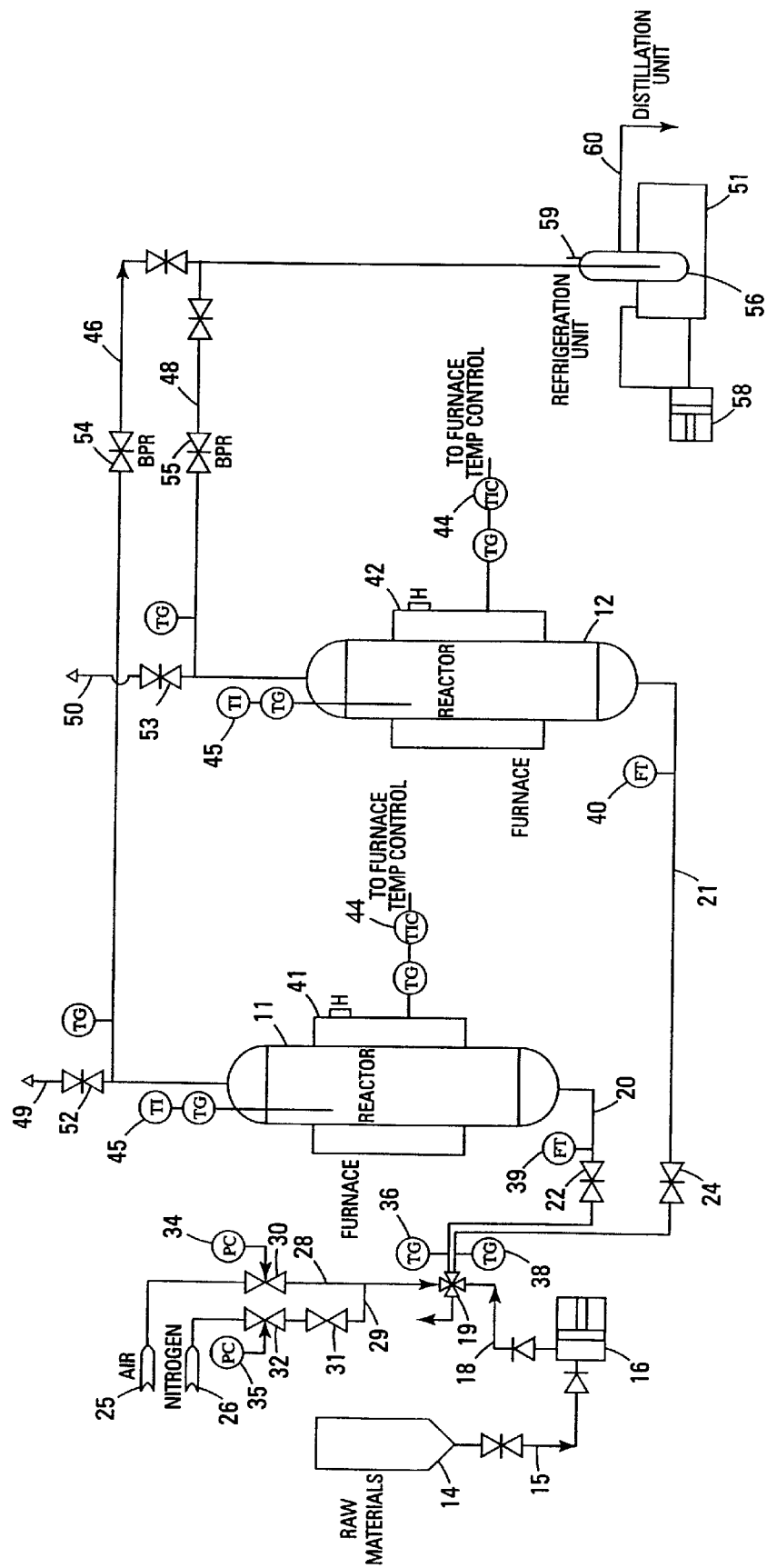

Reference is first made to the drawing which illustrates a schematic of the system or apparatus of the present invention and a flow diagram of the process in accordance with the present invention. While the apparatus and method are applicable to a wide variety of ketones and more specifically unsymmetrical ketones, they are particularly applicable to methyl cyclopropyl ketone (MCPK). Accordingly, the preferred embodiment and method will be described with respect to MCPK and a system and process used to make MCPK. Unless otherwise indicated all percentages are by weight.

In the drawing, the primary reaction members comprise a pair of vapor phase tube reactors 11 and 12. If desired or needed, more than two reactors could be provided to accommodate the specific reaction time or life cycle of the selected feed materials and the regeneration time of the selected catalyst. These reactors 11 and 12 are preferably conventional stainless steel catalytic tube reactors which are filled with various combinations of an inert filler material and a catalyst. In the preferred embodiment, the inert filler material is comprised of glass beads between about 3–10 mm in diameter, although it is contemplated that various other materials can be used as well such as stainless steel beads, lava rock and sand, among possible others. A portion of the reactors are also filled with a catalytic material to promote the desired reaction of the reactant materials. A variety of catalysts known in the art are useful in the production of ketones. These preferably include a catalyst carrier or support, which has been impregnated with a catalyst. Possible supports include metal or metal oxides such as alumina, silica, titania, zirconia and mixtures thereof and naturally occurring clay material such as montmorillonite or kaolin. Possible catalysts include, but are not limited to, metal or metal oxides such as oxides of cerium ($CeO_2$ or $CeO_3$), zirconium ($ZrO_2$), or other lanthanides, and the group III B, IV B and V B metal or metal oxides. The preferred catalysts are cerium oxide ($CeO_2$ or $CeO_3$), zirconium oxide ($ZrO_2$) or zinc oxide ($ZnO$). In the preferred method of the present invention, the catalytic material is $CeO_2$ provided on an aluminum oxide ($Al_2O_3$) or a zirconium support oxide ($ZrO_2$) support material.

One method of preparing the catalyst in accordance with the invention is by impregnating the porous support material with cerium acetate hydrate, $Ce(O_2CCH_3)_3 \cdot 1.5H_2O$. This gives 1.0 g of $CeO_2/2.0$ g of this precursor. The hydrate is dissolved as 200 g/L aqueous solution. The catalyst support is dried at 450 C. for twelve (12) hours. Impregnation is by the incipient wetness method (drop-wise), at ambient temperature. The aqueous solution can be divided to obtain the actual amount of catalyst necessary for the impregnation. Odd percentages can be obtained by using 10 milliliters of the solution for each one (1) gram of actual catalyst needed. For 5 wt% $CeO_2$ catalyst, 50 milliliters of this saturated aqueous solution is used per 100 grams of catalyst support. For impregnation of catalyst on the catalyst support greater than 5%, multiple applications should be used, with an intermediate drying step at 120 C., to insure uniform coverage. For 10 wt% $CeO_2$ catalyst, two (2) 50 milliliter solutions are used. The resulting catalyst support with impregnated catalyst is then oven-dried at 450 C. for twelve (12) hours, prior to pretreatment in the reactor. Other precursors, such as cerium nitrate and techniques, such as spray or tumble-drying, known to those skilled in the art, can be used to apply the catalyst.

The concentration of the catalyst in the reactors 11 and 12 is preferably in the range of 1 to 25 percent by weight, with the preferred range being 1 to 20 percent by weight. Such catalyst range, however, will vary with the particular catalyst and catalyst support and support configuration being used. For example, with a $CeO_2$ catalyst on a $Al_2O_3$ support having an exposed or effective surface area of about 178 $m^2/g$, the preferred range is 10 to 20% and more preferably 15 to 20%. For a $CeO_2$ catalyst on a $ZrO_2$ support having an exposed or effective surface area of about 34 $m^2/g$, the preferred range is less than 5% and more preferably about 2 to 5%.

The distribution of the catalyst within the reactors 11 and 12 can vary. Preferably, however, the bottom ⅓ of the reactor is filled with inert material in the form of glass beads, the middle third of the reactor is filled with catalyst and the top ⅓ of the reactor could be empty or filled with inert material in the form of glass beads.

In the preferred embodiment as shown, the reactors 11 and 12 are vertically oriented so that the feed materials pass vertically upwardly from the bottom to the top of the reactors. However, the benefits of the invention can also be realized with reactors having different orientations so that the feed materials flow downwardly or laterally through the reactors. These latter orientations are not as preferred, however, because of an increased tendency to plug.

The raw or reactive materials in accordance with the present invention are provided from a reactant material source or reservoir 14. In general, these reactant or feed materials will comprise a mixture of (1) a carboxylic acid or aldehyde or their derivatives and (2) a second carboxylic acid or its derivatives. As used herein, a derivative is a chemical substance or compound which is derived from another. For example, because the OH of a carboxylic acid can be replaced by a number of groups such as Cl, H, OR or $NH_2$ to yield acid chlorides, aldehydes, esters and amines, respectively, these are all considered derivatives of carboxylic acid. In the preferred embodiment, the reactant materials comprise a mixture of acetic acid and cyclopropylaldehyde or its derivatives (such as cyclopropanecarboxylic acid). The molar ratio of the acetic acid to the cyclopropanecarboxylic acid which makes up the feed stream or feed material is preferably in the range of 2:1 to 20:1. More preferably, the ratio of acetic acid to cyclopropanecarboxylic acid is about 3:1 to 8:1 and most preferably within arange of 3:1 to 5:1. The most preferred ratio is about 4:1. If desired, the feed materials can be provided in separate reservoirs or from separate sources and then combined in the desired feed ratio.

The feed material is fed from the reservoir 14 through a conduit 15 to a pump or pressure member 16 which discharges the feed material into the conduit 18 at an elevated pressure greater than atmospheric. The pressure is selected to optimize the reaction conditions (conversion and selectivity) and to maintain the feed materials in a gaseous state at the selected reaction temperature. In the preferred method and apparatus, the feed material is pressurized to a range of about 10 psig to about 200 psig, and more preferably to a pressure of about 20 psig to 100 psig. Most preferably, the pressure is provided at about 40 psig to 50 psig.

From the pump 16, the feed material is directed through the conduit 18 to a valve complex 19, which selectively directs the feed material either to the reactor feed conduit 20 or the reactor feed conduit 21. As shown, the feed conduits 20 and 21 are connected respectively, to the bottom ends of the reactors 11 and 12. The reactor feed conduits 20 and 21 include shutoff valves 22 and 24, respectively, for isolating the reactors 11 and 12 from the feed materials and facilitating the flow of purging or other materials, if desired. If more than two reactors are utilized, the valve complex 19 is modified and additional reactor feed conduits and shutoff valves are provided so that the flow of the feed materials can be selectively directed to each reactor, while selectively isolating one or more of the others.

The system of the present invention also includes a supply of purging and/or regeneration materials 25 and 26. Such materials may be provided from any available source such as a reservoir or the like. In the preferred embodiment, the materials 25 and 26 comprise air and nitrogen, respectively, although other materials known in the art can be used as well such as hydrogen and methane. The materials are used during purging or preheating of the reactors 11 or 12 or during regeneration of the catalyst within the reactors 11 and 12. The materials 25 and 26 are provided to the valve 19 through the conduits 28 and 29, respectively. The conduits 28 and 29 are also provided with a plurality of shut-off valves 30, 31 and 32 to selectively control the flow of materials 25 and 26 to the valve 19. Pressure regulators 34 and 35 are associated with the valves 30 and 32. The valve 19 functions to selectively direct the flow of materials 25 and/or 26 to either the reactor feed conduit 20 or the reactor feed conduit 21. The conduits 20 and 21 are provided with temperature gauges 36 and 38, respectively, upstream of the valves 22 and 24 The reactors 11 and 12 are also provided with heating means 41 and 42 and means in the form of the temperature control and regulators 44 for selectively controlling the heaters 41 and 42. Means for monitoring the temperature and pressure within the reactor are also provided on each reactor 11 and 12 in the form of the pressure and temperature monitors 45.

Outflow or product exit conduits 46 and 48 are connected with the top or upper ends of the reactors 11 and 12, respectively, for directing the outflow from the reactors to a product separation means 51. Connected with each of the conduits 46 and 48 is a secondary or waste conduit 49 and 50, respectively, for purging or regeneration material, which is not desired to be, directed to the recovery means 51. Appropriate valves 52, 53, 54 and 55 are provided in the conduits 49, 50, 46 and 48, respectively, for controlling the flow of the product and waste streams. If more than two reactors are provided, additional exit conduits, waste conduits and associated valves are also provided.

The product recovery means 51 includes a receiver, a precipitation or distillation column 56 and a pressure means or pump 58 to recover the preferred product, namely, methyl cyclopropyl ketone (MCPK) from the exit stream. In FIG. 1, the MCPK is recovered through the conduit 60, with the other materials or co-products being recovered through the conduit 59.

Having described the apparatus and system of the present invention in detail, the ketone production method may be understood best as follows. First, one of the reactors 11 and 12 is selected for initial use in the process of the present invention. For purposes of describing the preferred method of the present invention, the reactor 11 will be selected. In such case, the other reactor 12 is isolated from the system by closing the valves 24, 53 and 55. The reactor 11 is then prepared for preparation of the ketone, specifically MCPK, by activating the heater 41 and providing a purging gas from the sources 25 and/or 26, through the valve 19 and into the lower end of the reactor 11. In accordance with the preferred method, the reactor 11 is preheated by the heater 41 to a temperature in the range of 350° C. to 500° C. and more preferably in the range of 400° C. to 440° C. Most preferably, in accordance with the present invention, the preferred reaction temperature is first determined and the reactor is heated to this temperature. This preferred temperature will vary to some extent with the composition of the feed stream, the concentration and type of catalyst, the liquid or weight hourly space velocity at which the reactor will be run, etc. The reactor 11 is then heated to this preferred temperature.

When the preferred temperature is reached, the valve 19 is actuated to stop the flow of the purging or other gas to the reactor 11 and to provide feed material of the desired composition from the reservoir or source 14. In the preferred embodiment, this feed material is a mixture of acetic acid and cyclopropanecarboxylic acid in the ratios set forth above. This pressurized feed stream is supplied to the bottom of the reactor 11 so that the vaporized feed materials enter the reactor from the bottom and flow upwardly through the glass beads, the catalyst and the glass beads before exiting through the top of the reactor 11. During this process, the material in the feed stream and the conduit 20 is sufficiently pressurized as set forth above by the pressure means 16 to maintain the feed materials in a gaseous state at the reaction temperature. The feed materials are fed through the reactor 11 at a rate sufficient to provide a liquid or weight hourly space velocity in excess of 1, more preferably in excess of 2 and most preferably in the range of 5–20 or 10–20. As used herein and as known in the art, weight (or liquid) hourly space velocity (WHSV or LHSV) is the amount of raw material (unit weight or volume) per unit weight or volume of catalyst per hour.

During the passage of feed materials through the reactors, the temperature within the reactors is maintained at the preferred temperature. This temperature will vary depending upon the feed materials, the ketone being produced and the pressure within the reactors, among other possible factors. In general, the temperature and pressure are selected to achieve a desired reaction yield and to maintain the feed reactants in their gaseous form. Normally, the reaction temperatures for ketone produciton will be in the range of 100° C. to 500° C. For a MCPK production process, the reaction temperature will be in the range of 350° C. to 500° C. and more preferably 400° C. to 440° C.

Within the reactor 11, the feed material reacts in the presence of the catalyst and at the preferred temperature, to produce MCPK or other desired ketone along with other byproducts or co-products including acetone and dicyclopropyl ketone. With the valve 52 closed and the valve 54 open, this exit or product stream is then directed via the conduit 46 to the recovery means 51 where the MCPK and other co-products are separated from one another. Preferably, this separation/recovery process is a precipitation or distillation process known in the art.

With the method and apparatus as described above, conversion rates in excess of 80% can be achieved with conversion rates commonly in the range of 95%–99%. Also, with the above method and apparatus, selectivity of the converted feed stream to MCPK in excess of 50% and commonly in the range of 70%–80% can be achieved.

In the event the reactor 11 requires maintenance or for some reason the reactor becomes plugged or the catalyst needs regeneration, the second reactor 12 can be quickly and easily utilized without resulting in downtime and thus loss of production or production rate. To accomplish this conversion to the reactor 12, the reactor 12 can be brought up to the optimum temperature and the valve 24 can be opened to allow the flow of purging or other gas into the bottom of the reactor 12 through the reactor and out through the conduit 50. Once the optimum temperature has been reached and the reactor 12 has been sufficiently purged, the valve 19 is adjusted to direct the feed material from the reservoir 14 into and through the conduit 21 and through the reactor 12. When this is done, the valves 53 and 54 are closed and the valve 55 is opened. The previously used reactor 11 is then isolated from the feed materials and can be isolated entirely from the system by closing the valve 22 or can be provided with purging or regeneration material from the sources 25 and 26 if desired.

In the MCPK process of the preferred embodiment, the reaction time or reaction life cycle is greater than the catalyst regeneration time. Thus, a pair of reactors 11 and 12 is sufficient to provide a continuous ketone production process. As used herein, the term "reaction time" or "reaction life cycle" is the time during which acceptable reaction conditions exist (i.e., before catalyst regeneration is needed or plugging occurs) for the selected feed materials and selected catalyst at the specific reaction variables of temperature, pressure, WHSV and the like. The term "regeneration time" is the time needed to regenerate the selected catalyst. If the specific feed materials, catalyst and reaction variables are such that the reaction time or life cycle is less than the regeneration time. More than two reactors are needed to maintain a continuous ketone production process.

Having described the method and apparatus of the present invention in detail, the present invention can be further understood by reference to the following examples.

EXAMPLES

Results of examples are shown in Tables 1 and 2 below for various feed composition ratios, operating temperatures and pressures and weight hourly space velocities and at various concentrations of catalysts. Specifically, Table 1 reflects a 10 percent $CeO_2/Al_2O_3$ catalyst, while Table 2 reflects a 15 percent $CeO_2/Al_2O_3$ catalyst.

In the examples for the data in Tables 1 and 2, ½ inch I.D. stainless steel tube reactors were filled with glass beads, $CeO_2/Al_2O_3$ catalyst, and glass beads (of approximately ⅓, ⅓, ⅓). The reactor was preheated with flowing air at a temperature of 520 to 560 C. An internal thermocouple was located at the catalyst bed for monitoring the temperature. A standard controller was used for temperature control of the surrounding clamshell furnace and pressure was controlled using a diaphragm-type backpressure regulator.

Feed material in a molar ratio of 4:1 (acetic acid:cyclopropanecarboxylic acid) was fed into the reactor. For each example, the temperature, pressure and weight hourly space velocity was controlled to maintain "steady state" operation. Samples were taken from the output of the reactor and analyzed for cyclopropanecarboxylic acid (CPA) and MCPK for the purpose of calculating conversion and selectivity.

The $CeO_2$ containing catalyst was prepared by impregnating $Al_2O_3$ with cerium acetate hydrate via the incipient wetness method (drop-wise) at ambient temperature. The support was dried at 450 C. for eight (8) hours. For the five weight percent $CeO_2$ catalyst one solution was used, for the ten weight percent $CeO_2$ catalyst, two solutions were used, and for the fifteen weight percent $CeO_2$ catalyst, three solutions were used, each with an intermediate drying step at 120 C. The catalyst was then oven dried on the support at 450 C. for eight (8) hours prior to pre-treatment in the reactor.

The results were as follows:

TABLE 1

| Example No. | Molar Ratio | Temperature C. | Pressure psig | WHSV | Conversion CCA % | Selectivity MCPK % |
| --- | --- | --- | --- | --- | --- | --- |
| M-11-1A | 4:1 | 421 | 15 | 6–7 | 92 | 79 |
| M-11-6A | 4:1 | 435 | 35 | 5–6 | 91 | 62 |
| M-11-7A | 4:1 | 431 | 44 | 3–4 | 98 | 64 |
| M-11-8A | 4:1 | 431 | 52 | 3–4 | 98 | 70 |
| M-11-9A | 4:1 | 434 | 59 | 2–3 | 99 | 67 |
| M-11-12B | 4:1 | 433 | 48 | 3–4 | 96 | 76 |

10% $CeO_2/Al_2O_3$ (Engelhard)    Pretreated at 560 C., (Flowing Air)

TABLE 2

| Example No. | Molar Ratio | Temperature C. | Pressure psig | WHSV | Conversion CCA % | Selectivity MCPK % |
| --- | --- | --- | --- | --- | --- | --- |
| M-50-48 | 4:1 | 430 | 40 | 5–6 | 94 | 50 |
| M-50-64 | 4:1 | 405 | 40 | 5–6 | 99 | 70 |
| M-50-80 | 4:1 | 410 | 40 | 2–4 | 99 | 65 |
| M-50-96 | 4:1 | 405 | 40 | 4 | 98 | 72 |
| M-50-112 | 4:1 | 420 | 40 | 6–8 | 99 | 71 |

TABLE 2-continued

| Example No. | Molar Ratio | Temperature C. | Pressure psig | WHSV | Conversion CCA % | Selectivity MCPK % |
|---|---|---|---|---|---|---|
| M-50-128 | 4:1 | 410 | 40 | 6–8 | 96 | 72 |
| M-50-144 | 4:1 | 440 | 40 | 13–16 | 95 | 68 |

15% $CeO_2/Al_2O_3$ (Engelhard)  Pretreated at 520 C., (Flowing Air)
Ratio: Acetic Acid:Cyclopropanecarboxylic Acid
WHSV: (Weight Hourly Space Velocity) Grams Raw Material per Gram Catalyst per Hour
CCA: Cyclopropanecarboxylic Acid
MCPK: Methyl Cyclopropyl Ketone In the examples for the data in Tables 3, 4 and 5, yield data (conversion and selectivity is shown for a $CeO_2/ZrO_2$ catalyst structure of 2%, 3% and 4%. In these examples, the temperature was in the range of 410–450 C., the pressure was about 30 psig and the feed ratio of acetic acid to cyclopropanecarboxylic acid was 4:1. The other reaction conditions and equipment were similar to that of the $CeO_2/Al_2O_3$ example above.

TABLE 3

2% $CeO_2/ZrO_2$

| WHSV | Conversion $R_1M$ % | Selectivity $USK_1$ % |
|---|---|---|
| 2 | 78 | 60 |
| 4 | 87 | 74 |
| 6 | 85 | 72 |
| 8 | 82 | 65 |
| 10 | 75 | 55 |

TABLE 4

3% $CeO_2/ZrO_2$

| WHSV | Conversion $R_1M$ % | Selectivity $USK_1$ % |
|---|---|---|
| 2 | 86 | 82 |
| 4 | 90 | 83 |
| 6 | 91 | 85 |
| 8 | 91 | 86 |
| 10 | 92 | 83 |

TABLE 5

4% $CeO_2/ZrO_2$

| WHSV | Conversion $R_1M$ % | Selectivity $USK_1$ % |
|---|---|---|
| 2 | 78 | 55 |
| 4 | 82 | 62 |
| 6 | 84 | 63 |
| 8 | 86 | 68 |
| 10 | 80 | 62 |

The ketones produced by the apparatus and method of the present invention can be utilized and combined with other processes to produce various herbicidal or other agricultural compounds. Preferably, the ketone production method of the present invention can be used, in combination with other process steps, to prepare such a compound of the formula (I)

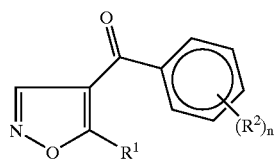

(I)

wherein:
$R^1$ is cycloalkyl having from three to six ring carbon atoms which is unsubstituted or which has one or more substituents selected from the group consisting of $R^4$ and halogen;

$R^2$ is halogen; straight- or branched-chain alkyl having up to six carbon atoms which is substituted by one or more $—OR^5$; cycloalkyl having from three to six carbon atoms; or a member selected from the group consisting of nitro, cyano, $—CO_2R^5$, $—NR^5R^6$, $—S(O)_pR^7$, $—O(CH_2)_mOR^5$, $—COR^5$, $—N(R^8)SO_2R^7$, $—OR^7$, $—OH$, $—OSO_2R^7$, $—(CR_9R^{10})_tSO_qR^{7a}$, $—CONR^5R^6$, $—N(R^8)—C(Z)Y$, $—(CR^9R^{10})NR^8R^{11}$ and $R^4$;

n is zero or an integer from one to three; when n is greater than one, then the groups $R^2$ are the same or different;

m is one, two or three;

p is zero, one or two;

q is zero, one or two;

t is an integer from one to four;

$R^3$ is straight- or branched-chain alkyl group containing up to six carbon atoms which is unsubstituted or which has one or more substituents selected from the group consisting of halogen, $—OR^5$, $—CO_2R^5$, $—S(O)_pR^7$, phenyl or cyano; or phenyl which is unsubstituted or which has one or more substituents selected from the group consisting of halogen, $—OR^5$ and $R^4$;

$R^4$ is straight- or branched-chain alkyl, alkenyl or alkynyl having up to six carbon atoms which is unsubstituted or is substituted by one or more halogen;

$R^5$ and $R^6$, which are the same or different, are each hydrogen or $R^4$;

$R^7$ and $R^{7a}$ independently are $R^4$, cycloalkyl having from three to six ring carbon atoms, or $—(CH_2)_w$-phenyl wherein phenyl is unsubstituted or is substituted by from one to five $R^{12}$ which are the same or different;

w is zero or one;

$R^8$ is hydrogen; straight- or branched-chain alkyl, alkenyl or alkynyl having up to ten carbon atoms which is unsubstituted or is substituted by one or more halogen; cycloalkyl having from three to six ring carbon atoms; $—(CH_2)_w$-phenyl wherein phenyl is unsubstituted or is substituted by from one to five $R^{12}$ which are the same or different; or $—OR^{13}$;

$R^9$ and $R^{10}$ independently are hydrogen or straight- or branched-chain alkyl having up to six carbon atoms which is unsubstituted or is substituted by one or more halogen;

$R^{11}$ is —$S(O)_qR^7$ or —$C(Z)Y$;

$R^{12}$ is halogen; straight- or branched-chain alkyl having up to three carbon atoms which is unsubstituted or is substituted by one or more halogen; or a member selected from the group consisting of nitro, cyano, —$S(O)_pR^3$ and —$OR^5$;

Y is oxygen or sulphur;

Z is $R^4$, —$NR^8R^{13}$, —$NR^8$—$NR^{13}R^{14}$, —$SR^7$ or —$OR^7$; and $R^{13}$ and $R^{14}$ independently are $R^8$, or an agriculturally acceptable salt or metal complex thereof, The process for preparing a compound of the above formula (I) comprises:

(i) reacting a compound of formula (II)

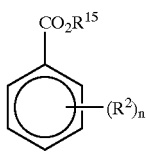
(II)

wherein $R^{15}$ is a straight- or branched-chain alkyl group having up to six carbon atoms with a compound of formula (III)

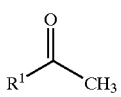
(III)

in an aprotic solvent in the absence of a base to form a compound of formula (IV)

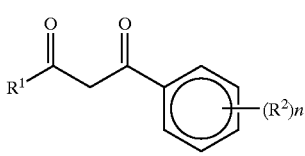
(IV)

(ii) reacting a compound of formula (IV) with a compound that contains a leaving group L such as alkoxy or N,N-dialkylamino, esp. ethoxy and $CH(OCH_2CH_3)_3$ to form a compound of formula (V)

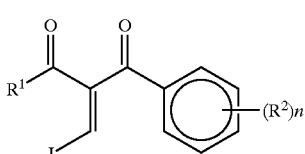
(V)

(iii) reacting a compound of formula (V) with hydroxylamine or a salt of hydroxylamine to form a compound of formula (I), wherein the process further comprises producing the compound of formula (III) by:

providing a catalytic bed;

providing a raw material feed comprised of a $R^1COOH$ or $R^1COH$ and a second carboxylic acid in the ratio of from 1:2 to 1:20;

passing said raw material feed through said catalytic bed at a temperature of between about 350° C. and 500° C. at a weight hourly space velocity greater than two; and separating the compound of formula (III).

In the above process, the compound of formula (III) is a ketone produced in accordance with the ketone production method of the present invention.

The ketone production method of the present invention can also be used, in combination with other process steps, to prepare a compound of the following formula (X)

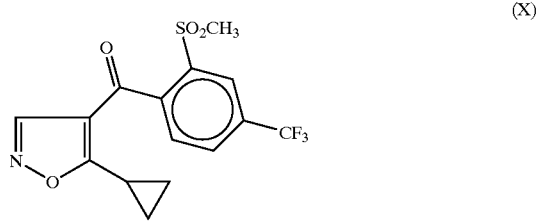
(X)

The specific process steps comprise:

(i) reacting a compound of formula (XI)

(XI)

with a compound of formula (XII)

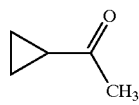
(XII)

to form a compound of formula (XIII)

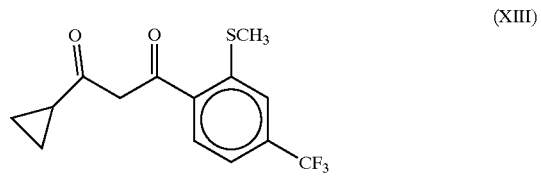
(XIII)

(ii) reacting a compound of formula (XIII) with $CH(OCH_2CH_3)_3$ to form a compound of formula (XIV)

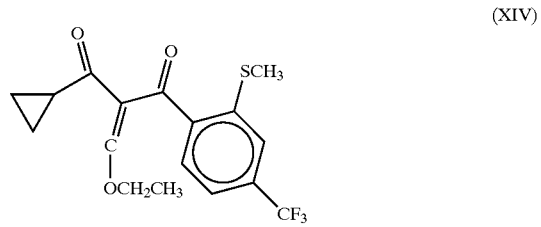
(XIV)

13

(iii) reacting a compound of formula (XIV) with hydroxylamine or a salt of hydroxylamine to form a compound of the formula (XV)

(XV)

(iv) reacting a compound of formula (XV) with chloroperbenzoic acid or an equivalent to form a compound of the formula (X)
wherein the process further comprises producing the compound of formula (XII) by:
providing a catalytic bed;
providing a raw material feed comprised of cyclopropane carboxylic acid or cyclopropane aldehyde and acetic acid in the ratio of from 1:2 to 1:20;
passing said raw material feed through said catalytic bed at a temperature of between about 350° C. and 500° C. at a weight hourly space velocity greater than two; and
separating the compound of formula (XII).

In the above process, the compound of formula (XII) is methyl cyclopropyl ketone (MCPK) produced in accordance with the ketone production method of the present invention.

Further details of compounds of formula (I) and formula (X) described above are known in the art and described in one or more of PCT Publication No. WO 99/02476, U.S. Pat. No. 5,366,957 and U.S. Pat. No. 5,849,928, the substance of which is incorporated herein by reference.

Although the description of the preferred embodiment and method have been quite specific, it is contemplated that various modifications could be made without deviating from the spirit of the present invention. Accordingly, it is intended that the scope of the present invention be dictated by the appended claims rather than by the description of the preferred embodiment.

What is claimed is:

1. A process for the preparation of a compound of formula (I)

(I)

wherein:
$R^1$ is cycloalkyl having from three to six ring carbon atoms which is unsubstituted or which has one or more substituents selected from the group consisting of $R^4$ and halogen;
$R^2$ is halogen; straight- or branched-chain alkyl having up to six carbon atoms which is substituted by one or more —$OR^5$; cycloalkyl having from three to six carbon atoms; or a member selected from the group consisting of nitro, cyano, —$CO_2R^5$, —$NR^5R^6$, —$S(O)_pR^7$, —$O(CH_2)_mOR^5$, —$COR^5$, —$N(R^8)SO_2R^7$, —$OR^7$, —OH, —$OSO_2R^7$, —$(CR_9R^{10})_tSO_qR^{7a}$, —$CONR^5R^6$, —$N(R^8)$—$C(Z)Y$, —$(CR^9R^{10})NR^8R^{11}$ and $R^4$;

14 n is zero or an integer from one to three; when n is greater than one, then the groups $R^2$ are the same or different;
m is one, two or three;
p is zero, one or two;
q is zero, one or two;
t is an integer from one to four;
$R^3$ is straight- or branched-chain alkyl group containing up to six carbon atoms which is unsubstituted or which has one or more substituents selected from the group consisting of halogen, —$OR^5$, —$CO_2R^5$, —$S(O)_pR^7$, phenyl or cyano; or phenyl which is unsubstituted or which has one or more substituents selected from the group consisting of halogen, —$OR^5$ and $R^4$;
$R^4$ is straight- or branched-chain alkyl, alkenyl or alkynyl having up to six carbon atoms which is unsubstituted or is substituted by one or more halogen;
$R^5$ and $R^6$, which are the same or different, are each hydrogen or $R^4$;
$R^7$ and $R^{7a}$ independently are $R^4$, cycloalkyl having from three to six ring carbon atoms, or —$(CH_2)_w$-phenyl wherein phenyl is unsubstituted or is substituted by from one to five $R^{12}$ which are the same or different;
w is zero or one;
$R^8$ is hydrogen; straight- or branched-chain alkyl, alkenyl or alkynyl having up to ten carbon atoms which is unsubstituted or is substituted by one or more halogen; cycloalkyl having from three to six ring carbon atoms; —$(CH_2)_w$-phenyl wherein phenyl is unsubstituted or is substituted by from one to five $R^{12}$ which are the same or different; or —$OR^{13}$;
$R^9$ and $R^{10}$ independently are hydrogen or straight- or branched-chain alkyl having up to six carbon atoms which is unsubstituted or is substituted by one or more halogen;
$R^{11}$ is —$S(O)_qR^7$ or —$C(Z)Y$;
$R^{12}$ is halogen; straight- or branched-chain alkyl having up to three carbon atoms which is unsubstituted or is substituted by one or more halogen; or a member selected from the group consisting of nitro, cyano, —$S(O)_pR^3$ and —$OR^5$;
Y is oxygen or sulphur;
Z is $R^4$, —$NR^8R^{13}$, —$NR^8$—$NR^{13}R^{14}$, —$SR^7$ or —$OR^7$; and
$R^{13}$ and $R^{14}$ independently are $R^8$,
or an agriculturally acceptable salt or metal complex thereof, which process comprises:
(i) reacting a compound of formula (II)

(II)

wherein $R^{15}$ is a straight- or branched-chain alkyl group having up to six carbon atoms with a compound of formula (III)

(III)

in an aprotic solvent in the absence of a bse to form a compound of formula (IV)

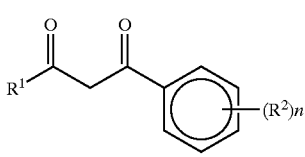

(IV)

(ii) reacting a compound of formula (IV) with a compound that contains a leaving group L to form a compound of formula (V)

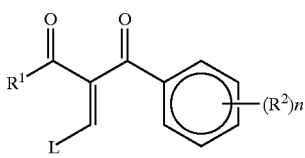

(V)

(iii) reacting a compound of formula (V) with hydroxylamine or a salt of hydroxylamine to form a compound of formula (I),
wherein the process further comprises producing the compound of formula (III) by:
providing a catalytic bed;
providing a raw material feed comprised of a $R^1COOH$ or $R^1COH$ and a second carboxylic acid in the ratio of from 1:2 to 1:20;
passing said raw material feed through said catalytic bed at a temperature of between about 350° C. and 500° C. at a weight hourly space velocity in the range of 5 to 20; and
separating the compound of formula (III).

2. The process of claim 1, wherein the second carboxylic acid is acetic acid.

3. The process of claim 1, comprising determining the preferred bed reaction temperature for said raw material feed and preheating said catalytic bed to said preferred bed reaction temperature.

4. The process of claim 1, wherein said ketone is an unsymmetrical ketone.

5. The process of claim 4, wherein said ketone is a cyclopropyl ketone and said aldehyde is cyclopropylaldehyde.

6. The process of claim 4, wherein said ketone is a cyclopropyl ketone and said first carboxylic acid is cyclopropanecarboxylic acid.

7. The process of claim 6, wherein said second carboxylic acid is acetic acid and said ketone is methyl cyclopropyl ketone.

8. the process of claim 1, wherein said catalytic bed comprises a $CeO_2/ZrO_2$ catalyst structure in the range of about 1 to 5% $CeO_2$ per gram of $ZrO_2$.

9. the process of claim 1, comprising maintaining said raw material feed in said catalytic bed at a pressure in range of 10 to 200 psi as said raw material passes through said catalytic bed.

10. The method of claim 1, wherein said first carboxylic acid and said second carboxylic acid are different.

11. A process for the preparation of a compound of formula (X)

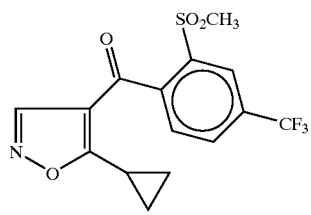

(X)

comprising:

(i) reacting a compound of formula (XI)

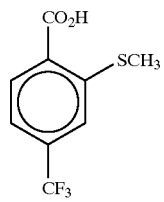

(XI)

with a compound of formula (XII)

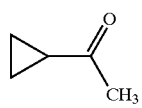

(XII)

to form a compound of formula (XIII)

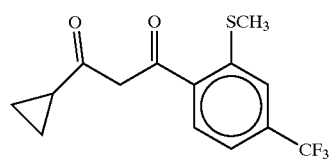

(XIII)

(ii) reacting a compound of formula (XIII) with $CH(OCH_2CH_3)_3$ to form a compound of formula (XIV)

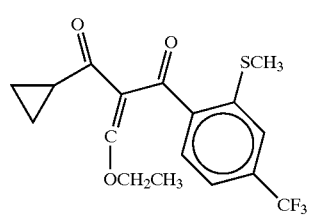

(XIV)

(iii) reacting a compound of formula (XIV) with hydroxylamine or a salt of hydroxylamine to form a compound of the formula (XV)

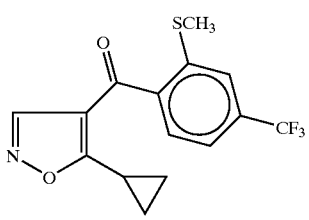

(iv) reacting a compound of formula (XV) with chloroperbenzoic acid to form a compound of the formula (X) wherein the process further comprises producing the compound of formula (XII) by:
providing a catalytic bed;
providing a raw material feed comprised of cyclopropane carboxylic acid or cyclopropane aldehyde and acetic acid in the ratio of from 1:2 to 1:20;
passing said raw material feed through said catalytic bed at a temperature of between about 350° C. and 500° C. at a weight hourly space velocity in the range of 5 to 20; and
separating the compound of formula (XII).

12. The process of claim 11, wherein the second carboxylic acid is acetic acid.

13. The process of claim 11, comprising determining the preferred bed reaction temperature for said raw material feed and preheating said catalytic bed to said preferred bed reaction temperature.

14. The process of claim 11, wherein said ketone is an unsymmetrical ketone.

15. The process of claim 14, wherein said ketone is a cyclopropyl ketone and said aldehyde is cyclopropylaldehyde.

16. The process of claim 14, wherein said ketone is a cyclopropyl ketone and said first carboxylic acid is cyclopropanecarboxylic acid.

17. The process of claim 16, wherein said second carboxylic acid is acetic acid and said ketone is methyl cyclopropyl ketone.

18. The process of claim 11, wherein said catalytic bed comprises a $CeO_2/ZrO_2$ catalyst structure in the range of about 1 to 5% $CeO_2$ per gram of $ZrO_2$.

19. The process of claim 11, comprising maintaining said raw material feed in said catalytic bed at a pressure in the range of 10 to 200 psi as said raw material passes through said catalytic bed.

20. The process of claim 11, wherein said first carboxylic acid and said second carboxylic acid are different.

21. A process for the preparation of a compound of formula (I)

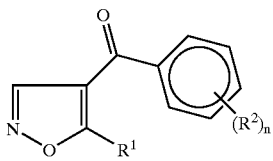

wherein:
$R^1$ is cycloalkyl having from three to six ring carbon atoms which is unsubstituted or which has one or more substituents selected from the group consisting of $R^4$ and halogen;

$R^2$ is halogen; straight- or branched-chain alkyl having up to six carbon atoms which is substituted by one or more $-OR^5$; cycloalkyl having from three to six carbon atoms; or a member selected from the group consisting of nitro, cyano, $-CO_2R^5$, $-NR^5R^6$, $-S(O)_pR^7$, $-O(CH_2)_mOR^5$, $-COR^5$, $-N(R^8)SO_2R^7$, $-OR^7$, $-OH$, $-OSO_2R^7$, $-(CR_5R^{10})_tSO_qR^{7a}$, $-CONR^5R^6$, $-N(R^8)-C(Z)Y$, $-(CR^9R^{10})NR^8R^{11}$ and $R^4$;

n is zero or an integer from one to three; when n is greater than one, then the groups $R^2$ are the same or different;

m is one, two or three;

p is zero, one or two;

q is zero, one or two;

t is an integer from one to four;

$R^3$ is straight- or branched-chain alkyl group containing up to six carbon atoms which is unsubstituted or which has one or more substituents selected from the group consisting of halogen, $-OR^5$, $-CO_2R^5$, $-S(O)_pR^7$, phenyl or cyano; or phenyl which is unsubstituted or which has one or more substituents selected from the group consisting of halogen, $-OR^5$ and $R^4$;

$R^4$ is straight- or branched-chain alkyl, alkenyl or alkynyl having up to six carbon atoms which is unsubstituted or is substituted by one or more halogen;

$R^5$ and $R^6$, which are the same or different, are each hydrogen or $R^4$;

$R^7$ and $R^{7a}$ independently are $R^4$, cycloalkyl having from three to six ring carbon atoms, or $-(CH_2)_w$-phenyl wherein phenyl is unsubstituted or is substituted by from one to five $R^{12}$ which are the same or different;

w is zero or one;

$R^8$ is hydrogen; straight- or branched-chain alkyl, alkenyl or alkynyl having up to ten carbon atoms which is unsubstituted or is substituted by one or more halogen; cycloalkyl having from three to six ring carbon atoms; $-(CH_2)_w$-phenyl wherein phenyl is unsubstituted or is substituted by from one to five $R^{12}$ which are the same or different; or $-OR^{13}$;

$R^9$ and $R^{10}$ independently are hydrogen or straight- or branched-chain alkyl having up to six carbon atoms which is unsubstituted or is substituted by one or more halogen;

$R^{11}$ is $-S(O)_qR^7$ or $-C(Z)Y$;

$R^{12}$ is halogen; straight- or branched-chain alkyl having up to three carbon atoms which is unsubstituted or is substituted by one or more halogen; or a member selected from the group consisting of nitro, cyano, $-S(O)_pR^3$ and $-OR^5$;

Y is oxygen or sulphur;

Z is $R^4$, $-NR^8R^{13}$, $-NR^8-NR^{13}R^{14}$, $-SR^7$ or $-OR^7$; and $R^{13}$ and $R^{14}$ independently are $R^8$, or an agriculturally acceptable salt or metal complex thereof, which process comprises:
(i) reacting a compound of formula (II)

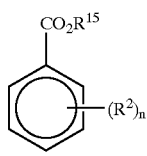

wherein $R^{15}$ is a straight- or branched-chain alkyl group having up to six carbon atoms with a compound of formula (III)

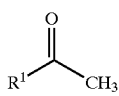
(III)

in an aprotic solvent in the absence of a base to form a compound of formula (IV)

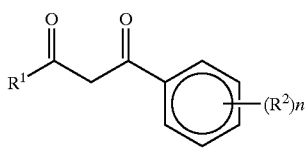
(IV)

(ii) reacting a compound of formula (IV) with a compound that contains a leaving group L to form a compound of formula (V)

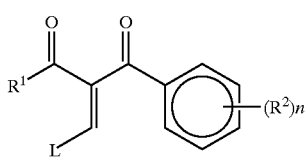
(V)

(iii) reacting a compound of formula (V) with hydroxylamine or a salt of hydroxylamine to form a compound of formula (I),
wherein the process further comprises producing the compound of formula (III) by:
providing a catalytic bed;
providing a raw material feed comprised of a $R^1COOH$ or $R^1COH$ and a of from 1:2 to 1:20;
passing said raw material feed through said catalytic bed at a temperature of between about 100° C. and 500° C. and at a pressure in the range of about 10 psig to about 200 psig and at a weight hourly space velocity in the range of 5 to 20; and
separating the compound of formula (III).

22. The process of claim 21, wherein said pressure is in the range of about 20 psig to 100 psig.

23. The process of claim 21, wherein the second carboxylic acid is acetic acid.

24. The process of claim 21, comprising determining the preferred bed reaction temperature for said raw material feed and preheating said catalytic bed to said preferred bed reaction temperature.

25. The process of claim 21, wherein said ketone is an unsymmetrical ketone.

26. The process of claim 25, wherein said ketone is a cyclopropyl ketone and said aldehyde is cyclopropylaldehyde.

27. The process of claim 25, wherein said ketone is a cyclopropyl ketone and said first carboxylic acid is cyclopropanecarboxylic acid.

28. The process of claim 27, wherein said second carboxylic acid is acetic acid and said ketone is methyl cyclopropyl ketone.

29. The process of claim 21, wherein said catalytic bed comprises a $CeO_2/ZrO_2$ catalyst structure in the range of about 1 to 5% $CeO_2$ per gram of $ZrO_2$.

30. The process of claim 21, comprising maintaining said raw material feed in said catalytic bed at a pressure in the range of 10 to 200 psi as said raw material passes through said catalytic bed.

31. The process of claim 21, wherein said first carboxylic acid and said second carboxylic acid are different.

32. A process for the preparation of a compound of formula (X)

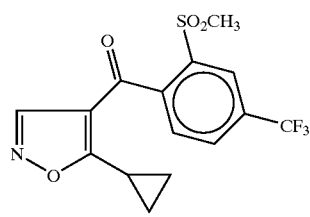
(X)

comprising:

(i) reacting a compound of formula (XI)

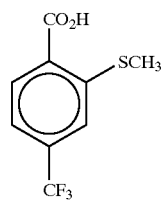
(XI)

with a compound of formula (XII)

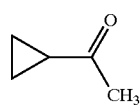
(XII)

to form a compound of formula (XIII)

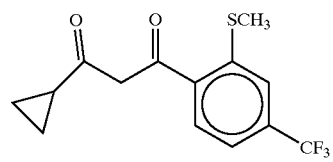
(XIII)

(ii) reacting a compound of formula (XIII) with $CH(OCH_2CH_3)_3$ to form a compound of formula (XIV)

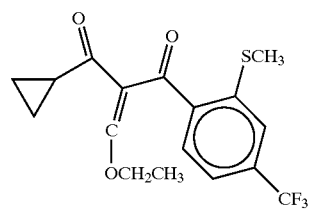
(XIV)

(iii) reacting a compound of formula (XIV) with hydroxylamine or a salt of hydroxylamine to form a compound of the formula (XV)

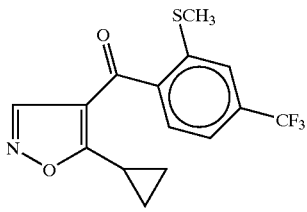

(XV)

(iv) reacting a compound of formula (XV) with chloroperbenzoic acid to form a compound of the formula (X) wherein the process further comprises producing the compound of formula (XII) by:
providing a catalytic bed;
providing a raw material feed comprised of cyclopropane carboxylic acid or cyclopropane aldehyde and acetic acid in the ratio of from 1:2 to 1:20;
passing said raw material feed through said catalytic bed at a temperature of between about 100° C. and 500° C. and at a pressure in the range of about 10 psig to about 200 psig and at a weight hourly space velocity in the range of 5 to 20; and
separating the compound of formula (XII).

33. The process of claim 32, wherein said pressure is in the range of about 20 psig to 100 psig.

34. The process of claim 32, wherein the second carboxylic acid is acetic acid.

35. The process of claim 32, comprising determining the preferred bed reaction temperature for said raw material feed and preheating said catalytic bed to said preferred bed reaction temperature.

36. The process of claim 32, wherein said ketone is an unsymmetrical ketone.

37. The process of claim 34, wherein said ketone is a cyclopropyl ketone and said aldehyde is cyclopropylaldehyde.

38. The process of claim 34, wherein said ketone is a cyclopropyl ketone and said first carboxylic acid is cyclopropanecarboxylic acid.

39. The process of claim 36, wherein said second carboxylic acid is acetic acid and said ketone is methyl cyclopropyl ketone.

40. The process of claim 32, wherein said catalytic bed comprises a $CeO_2/ZrO_2$ catalyst structure in the range of about 1 to 5% $CeO_2$ per gram of $ZrO_2$.

41. The process of claim 32, comprising maintaining said raw material feed in said catalytic bed at a pressure in the range of 10 to 200 psi as said raw material passes through said catalytic bed.

42. The process of claim 32, wherein said first carboxylic acid and said second carboxylic acid are different.

* * * * *